United States Patent
Kudaev et al.

(10) Patent No.: US 11,931,185 B2
(45) Date of Patent: Mar. 19, 2024

(54) VITAL SIGN SENSOR AND METHOD FOR MANUFACTURING A VITAL SIGN SENSOR

(71) Applicant: OSRAM Opto Semiconductors GmbH, Regensburg (DE)

(72) Inventors: Sergey Kudaev, Regensburg (DE); Reiner Windisch, Pettendorf (DE); Dennis Sprenger, Röthenbach (DE); Ralph Wirth, Lappersdorf (DE); Thomas Klafta, Burglengenfeld (DE)

(73) Assignee: OSRAM Opto Semiconductors GmbH, Regensburg (DE)

( * ) Notice: Subject to any disclaimer, the term of this patent is extended or adjusted under 35 U.S.C. 154(b) by 210 days.

(21) Appl. No.: 17/440,657

(22) PCT Filed: Mar. 24, 2020

(86) PCT No.: PCT/EP2020/058159
§ 371 (c)(1),
(2) Date: Sep. 17, 2021

(87) PCT Pub. No.: WO2020/193550
PCT Pub. Date: Oct. 1, 2020

(65) Prior Publication Data
US 2022/0151564 A1     May 19, 2022

(30) Foreign Application Priority Data

Mar. 26, 2019   (DE) .................. 10 2019 107 765.6

(51) Int. Cl.
*A61B 5/00* (2006.01)
*A61B 5/024* (2006.01)

(52) U.S. Cl.
CPC ........ *A61B 5/7207* (2013.01); *A61B 5/02427* (2013.01); *A61B 5/6801* (2013.01); *A61B 2562/12* (2013.01)

(58) Field of Classification Search
None
See application file for complete search history.

(56) References Cited

U.S. PATENT DOCUMENTS

| | | | |
|---|---|---|---|
| 2009/0152582 A1* | 6/2009 | Chang | H01L 33/507 257/E33.061 |
| 2013/0207148 A1 | 8/2013 | Krauter et al. | |
| 2016/0238440 A1 | 8/2016 | Chu et al. | |
| 2017/0028215 A1* | 2/2017 | Medendorp, Jr. | A61N 5/0603 |
| 2018/0000362 A1* | 1/2018 | Matsuo | A61B 5/02427 |

(Continued)

FOREIGN PATENT DOCUMENTS

| | | |
|---|---|---|
| DE | 102010034913 A1 | 2/2012 |
| DE | 102016104790 A1 | 9/2017 |

(Continued)

*Primary Examiner* — Yi-Shan Yang
(74) *Attorney, Agent, or Firm* — Slater Matsil, LLP (57) ABSTRACT

In an embodiment a vital sign sensor includes an emitter component configured to emit light, a detector component configured to detect light, a first layer of a substantially transparent material, wherein the emitter component is embedded in the first layer, and a second layer of a light scattering material arranged on the first layer, wherein the second layer includes converter particles, and wherein the first layer and the second layer are surrounded by at least one wall of a reflective material.

16 Claims, 4 Drawing Sheets

(56) References Cited

U.S. PATENT DOCUMENTS

| | | |
|---|---|---|
| 2018/0114875 A1 | 4/2018 | Ho et al. |
| 2018/0192901 A1 | 7/2018 | Koike |
| 2018/0261735 A1* | 9/2018 | Schwarz ............... H01L 33/505 |
| 2019/0088838 A1 | 3/2019 | Domann et al. |
| 2021/0373132 A1* | 12/2021 | Etschmaier ........... G01S 7/4813 |

FOREIGN PATENT DOCUMENTS

| | | |
|---|---|---|
| EP | 2214218 A2 | 8/2010 |
| WO | 2016087444 A1 | 6/2016 |

* cited by examiner

VITAL SIGN SENSOR AND METHOD FOR MANUFACTURING A VITAL SIGN SENSOR

This patent application is a national phase filing under section 371 of PCT/EP2020/058159, filed Mar. 24, 2020, which claims the priority of German patent application 102019107765.6, filed Mar. 26, 2019, each of which is incorporated herein by reference in its entirety.

TECHNICAL FIELD

The present invention relates to a vital sign sensor, a portable electronic device and a method for manufacturing a vital sign sensor.

BACKGROUND

Vital sign sensors, also called vital sign monitors, are sensors that can be placed on the skin of a human or animal and, if necessary, together with electronics, determine vital signs of the human or animal concerned. As a vital sign, for example, the heartbeat, the heartbeat frequency or the pulse of the human or animal can be measured by the vital sign sensor.

Figure 1:
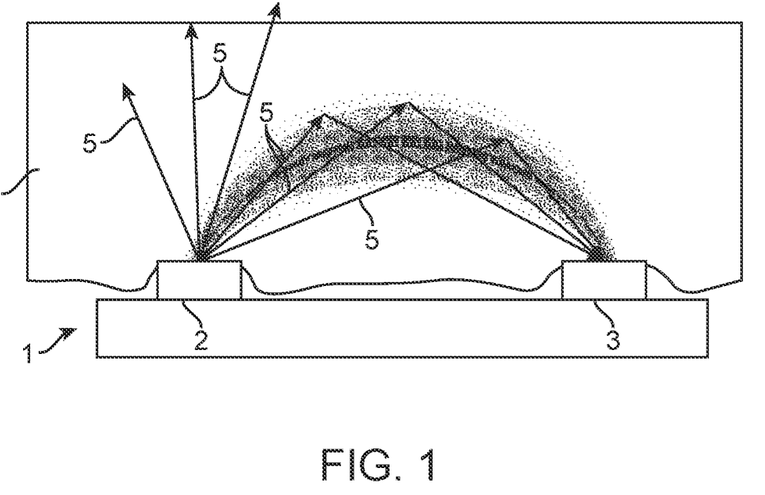
FIG. 1 is an illustration of a vital sign sensor with an emitter and a detector.

FIG. 1 schematically shows a vital sign sensor 1, which comprises an emitter 2 and a detector 3 and is placed on the skin 4 of a user. The light 5 emitted by the emitter 2, for example a light emitting diode (LED), propagates in the skin 4 and is partly absorbed by the blood in the blood vessels. The more blood interacts with the light 5, the more light 5 is absorbed. As a result, less light 5 reaches the detector 3, which is for example a photodiode, and the signal generated by the photodiode becomes smaller.

After each heartbeat, a pulse wave occurs in the vessels and the blood volume increases for a short time. At this moment, the detector 3 generates a smaller electrical signal compared to a time after the pulse wave. With each heartbeat, the cycle starts all over again. The periodic change in the signal output by the detector 3 is detected by subsequent electronics. The electronics calculate the heart rate from this, for example.

The emitter 2, designed as an LED, can emit red or green light 5, for example, which is coupled directly into the skin 4. Possible propagation paths A, B and C from the emitter 2 to the detector 3 are shown schematically in FIG. 2.

Figure 2:
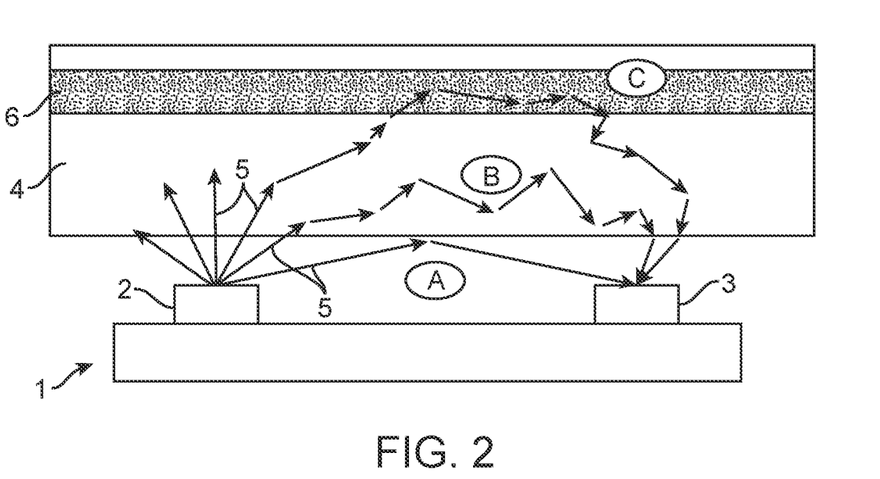
FIG. 2 is an illustration of possible propagation paths of the light from the emitter to the detector.

Path A results from a direct reflection of the light 5 at the skin surface.

Path B is caused by a scattering of the light 5 in the upper skin layers, which are less than 1 mmm deep below the skin surface.

Path C results from a scattering of light 5 in deeper skin layers that are at least 1 mm below the skin surface.

The density of blood vessels 6 in the upper skin layers is much smaller than inside the skin. Therefore, only the light 5 that penetrates deeper into the skin 4 and then reaches the detector 3 contains the information about the heart rate. The amount of light 5 that contains this information is approximately 1% to 2% of the total amount of light that falls on the detector 3.

The position of the vital sign sensor 1 relative to the skin 4 may change as the user moves. In particular, the ratios between the light quantities of the three light paths A, B and C mentioned above change. Furthermore, a change in position can cause the vital sign sensor 1 to be located directly opposite a large blood vessel for a short time, which causes a very strongly modulated signal. Assuming the vital sign sensor 1 moves shortly thereafter, creating an air gap between the vital sign sensor 1 and the skin 4, the modulated signal drops, but the light reflected from the skin surface produces a very strong non-modulated signal. Such artifacts caused by motion (motion artifacts) interfere with the evaluation algorithm and lead to inaccurate measurement of heart rate.

SUMMARY

Embodiments provide a vital sign sensor that has a lower sensitivity to motion artifacts and a better reproducibility of the measured signal. Other embodiments provide a portable electronic device with such a vital sign sensor. Further embodiments provide a method for manufacturing a vital sign sensor.

A vital sign sensor comprises at least one emitter component configured to emit light during operation of the vital sign sensor, and at least one detector component configured to detect light, in particular the light emitted by the emitter component, during operation of the vital sign sensor. Further, the vital sign sensor comprises a first layer of a substantially transparent material and a second layer of a light scattering material arranged on the first layer. The emitter component is embedded in the first layer.

The emitter component may, for example, be a light emitting diode (LED), an organic light emitting diode (OLED), a light emitting transistor or an organic light emitting transistor. In various embodiments, the emitter component may be part of an integrated circuit. Further, the emitter component may be a semiconductor chip. The emitter component may be housed in the vital sign sensor in a cavity.

The light emitted from the emitter component may be, for example, visible light, ultraviolet (UV) light, and/or infrared (IR) light.

The detector component may be a photodiode. The detector component may be part of an integrated circuit. Furthermore, the emitter component may be a semiconductor chip. The detector component may be housed in the vital sign sensor in a separate cavity.

The first layer is made of a material that is at least partially transparent to the wavelength spectrum emitted by the emitter component. Further, the first layer causes substantially no scattering of light emitted from the emitter component as the light passes through the first layer. For example, the first layer may be made of a clear silicone or epoxy resin.

The first layer may be a potting compound that covers all exposed surfaces of the emitter component. For example, the emitter component may have a first main surface and a second main surface opposite the first main surface. Further, a plurality of side surfaces may extend from the first main surface to the second main surface. The emitter component may be mounted with its first main surface on a carrier. The exposed areas of the second main surface and the side surfaces of the emitter component may be completely covered by the first layer. Non-exposed areas of the second main surface may be, for example, areas to which a bonding wire is attached.

The detector component may also be embedded in a clear, non-light-scattering potting compound.

The clear, non-light-scattering potting compound can protect the emitter or detector component from mechanical damage.

The second layer of a light-scattering material can be arranged directly or firmly bonded on the first layer, i.e., there is no intermediate layer between the first and second layer. The second layer provides scattering for the light emitted by the emitter component. To achieve the desired light scattering, scattering particles and/or phosphor particles may be integrated into the second layer. As a carrier material, the second layer may, for example, comprise a silicone into which the scattering particles and/or phosphor particles are mixed.

The vital sign sensor can be designed in such a way that during operation of the vital sign sensor the second layer faces the user's skin.

The light generated by the emitter component may propagate within the first layer until it is coupled out via the light-scattering second layer. The emitter component can be, for example, a volume-emitting component, e.g., a volume-emitting sapphire chip, i.e., an InGaN chip with a sapphire substrate. Such a component emits a large portion of light approximately horizontally, i.e. parallel to the component surface. This light propagates laterally in the transparent first layer until it enters the light-scattering second layer and is coupled out from there. This effectively increases the area in which the light is emitted from the vital sign sensor, which has the effect of reducing motion artifacts and giving the measurement signal output from the detector component higher reproducibility.

When the vital sign sensor emits light from only a small area and an air gap is created between the vital sign sensor and the skin due to user movement, less light is coupled into the skin and the measurement signal decreases accordingly. In contrast, the increased emissive area of the vital sign sensor described in the present application has the advantage that if the vital sign sensor loses contact with the skin at one location, the vital sign sensor retains contact at another location and thus light continues to be coupled into the skin at this location, whereby the measurement signal is influenced to a significantly lesser extent.

Furthermore, sufficient reproducibility of the signal output by the detector component can be achieved with comparatively few emitter components, which means a reduction in cost.

Higher efficiency, as provided by the present vital sign sensor, is important for battery-powered applications such as wearables.

According to one embodiment, the second layer comprises an exposed surface that is larger than a main surface of the emitter component. The exposed surface of the second layer is the surface that faces away from the first layer and is visible to an observer from outside the vital sign sensor. For example, the exposed surface of the second layer may be larger than a main surface of the emitter component by at least a factor of 5 or 10 or 15 or 20. Accordingly, the vital sign sensor provides an increased effective emissive area that is substantially larger than the emitter component.

The refractive indices of the first layer and the second layer may be chosen differently. For example, the first, transparent layer may have a higher refractive index than the second, light-scattering layer. This results in waveguiding for part of the light by total reflection at the interface between the two layers, causing the light to propagate further laterally. In particular, a refractive index of greater than 1.5 at room temperature can be selected for the first layer and a refractive index of less than 1.45 at room temperature can be selected for the second layer. For example, the first layer may be manufactured of a clear silicone with a refractive index in the range of 1.52 to 1.55 at room temperature, and the second layer may comprise a silicone with a refractive index of about 1.42 at room temperature.

Advantageously, a higher refractive index of the first layer directly surrounding the emitter component leads to improved light extraction from the emitter component and thus to an increase in efficiency.

The second layer may comprise scattering particles that do not substantially absorb light emitted from the emitter component. For example, such scattering particles may consist of $Al_2O_3$ or $TiO_2$. If a green light-emitting InGaN sapphire chip is used as the emitter component, it is advantageous to integrate scattering particles made of $Al_2O_3$ and/or $TiO_2$ in the second layer.

Furthermore, it can be provided that converter particles are integrated into the second layer. The converter particles are configured to convert the light emitted by the emitter component into light of a different wavelength. In other words, in this case the second layer is configured to convert a primary radiation generated by the emitter component. Primary radiation entering the second layer is at least partially converted into secondary radiation by the converter particles and, in particular, scattered in the process. The secondary radiation comprises wavelengths which differ from the wavelengths of the primary radiation, i.e. which are longer or shorter than the wavelengths of the primary radiation.

The converter particles may be embedded in a different material or matrix, for example silicone.

Suitable phosphors for the converter particles include (nitride) orthosilicates, Lu-containing garnets, organic phosphors or quantum dot phosphors.

For example, a blue-emitting InGaN chip can be used as the emitter component, and the second, scattering layer can be filled with green-emitting phosphor particles that convert most of the incident blue light into green light. Since green-emitting LED chips generally have lower efficiencies than blue-emitting chips, higher emitter efficiencies can be achieved as a result. The two-layer design means that the green converted light is generated somewhat further away from the emitter component than in a classic volume encapsulation, which means that less green light is incident on the partially absorbing emitter component and the efficiency is thus additionally increased. The associated disadvantage of poorer cooling of the phosphor does not play a role in the small light outputs required by the vital sign sensor.

When the vital sign sensor is switched off, the emitter component is not visible to an observer. The observer sees only the homogeneous surface of the second layer, which may be white, for example, if the second layer contains only scattering particles, or greenish if the second layer contains respective converter particles. A homogeneous appearance of the surface of the vital sign sensor is often desired for design reasons.

Even if noticeable luminance variations occur over the surface of the second layer during a measurement, the entire surface appears to the human eye as a relatively uniformly illuminated area. This enables a design- or brand-specific configuration of this surface, i.e. when looking at the sensor, the user recognizes a luminous symbol that can be selected relatively freely by the manufacturer, for example a logo.

For efficient light propagation, a well-reflecting mounting plane of the emitter component is advantageous. Accordingly, the emitter component can be mounted on a carrier made of a light-reflecting material or coated with such a material.

At least the surface of the carrier facing the emitter component can be designed to be specularly reflective, for example by applying a silver layer to the carrier. Alternatively, the surface of the carrier can be designed to scatter light, for example as a white reflector consisting of a white potting or molding material, ceramic or $TiO_2$-filled silicone or epoxy resin. The reflectivity should be more than 90%, ideally about 95%.

If the same refractive indices are used for the first and second layer, the choice of reflector, i.e. specular or scattering, does not play a significant role, since there is no real waveguiding within the first layer anyway. If a material with a higher refractive index than the refractive index of the second layer is chosen for the first layer, a specular reflector has the advantage that part of the light is guided and is only coupled out at a diffusely reflecting side wall of the cavity in which the emitter component is housed, resulting in a broader light distribution.

A locally different mirror can also be used to control the light extraction. For example, the carrier can be coated with a specular reflector in the immediate vicinity of the emitter component and with a scattering reflector at a greater distance from the emitter component.

The carrier can further be formed as a printed circuit board. A printed circuit board is also known as a PCB, circuit card, circuit board or printed circuit. A printed circuit board comprises a body of electrically insulating material with conductor tracks adhering to it and, if necessary, through-platings. The conductor tracks can be used for electrical contacting of the emitter component as well as the detector component.

The vital sign sensor may comprise exactly one emitter component, but may also comprise multiple emitter components configured to emit light of a first wavelength spectrum. In particular, the emitter components may be identical in construction or at least of the same type such that they emit light with the same wavelength spectrum. Within the vital sign sensor, the emitter components can be positioned to optimize the homogeneity of the light emission. For example, the vital sign sensor may include four emitter components positioned along the edges of an imaginary rectangle or in the corners of an imaginary rectangle.

The vital sign sensor may further comprise one or more additional emitter components that emit light with a second wavelength spectrum that is different from the first wavelength spectrum. Such emitter components may be used for additional applications of the vital sign sensor, such as measuring oxygen saturation, hemoglobin, or humidity. For example, the further emitter components may emit red or infrared light. The further emitter components may be embedded in the first layer in the manner described above. As a result, the light from the additional emitter components is also emitted more homogeneously from the exposed surface of the second layer. This also applies in the case where a green phosphor is used, since this is a non-absorbing scattering particle for light with longer wavelengths than its emission wavelength. Functionally, therefore, the green phosphor acts as a conversion material for blue light and as a scatterer for red and infrared light.

The first layer and the second layer may be surrounded by one or more walls or dams of a reflective material. These walls may form a cavity in which the emitter component(s) are housed. In particular, the walls are diffusely reflective.

For example, one wall may form an outer ring and another wall may form an inner ring located within the outer ring. For example, the outer ring and the inner ring may be round or square or any other shape. The emitter component or components may be arranged in the region between the outer ring and the inner ring. This region may further be covered with the first and second layer. The detector component may be arranged within the inner ring.

A wall may be arranged between the emitter component and the detector component. The side of the wall facing the emitter component can be reflective, in particular diffusely reflective or specularly reflective. The side of the wall facing the detector component may be black to reflect as little stray light as possible onto the detector. For example, the wall can be of a reflective material and comprise a black layer on the side of the detector component. The wall between the emitter component and the detector component may be a portion of the at least one wall surrounding the first layer and the second layer. However, it may also be a different wall therefrom.

According to one embodiment, the vital sign sensor described above is integrated into a wearable electronic device. In particular, the wearable electronic device is a so-called wearable, which literally means "portable".

A wearable is worn on the user's body during use or is integrated into clothing. A wearable can be, for example, a smartwatch, a pair of data glasses, or an activity or fitness tracker.

The wearable electronic device may be attached, for example by means of a strap or wristband, to a body part of the user such that the second layer of the vital sign sensor integrated in the wearable electronic device faces the body part and, in particular, abuts the body part.

Furthermore, the vital sign sensor may also be integrated into a medical device and serve to record measurement data of a patient.

A method according to one embodiment is for manufacturing a vital sign sensor. The method comprises providing an emitter component for generating light and a detector component for detecting light. The emitter component is embedded in a first layer of a substantially transparent material, and a second layer of a light-scattering material is applied to the first layer.

The method of manufacturing a vital sign sensor may comprise the vital sign sensor embodiments described above.

The emitter component and the detector component may be applied to a carrier before the emitter component is embedded in the first layer. The carrier may in particular be a printed circuit board.

At least that surface of the carrier to which the emitter component is applied may be light reflective. For example, white solder resist may be applied to the carrier.

At least one wall of reflective material may be formed on the carrier to delimit a surface on the carrier. To generate the first layer, the material of the first layer may be casted onto the surface in a liquid state, with the at least one wall serving as a dam. Subsequently, the material solidifies.

The second layer may be formed by casting the material of the second layer in a liquid state onto the first layer, followed by solidification. The at least one wall again serves as a dam.

Alternatively, after the first layer has been generated, at least one further wall can be generated on the existing wall or elsewhere and then the material of the second layer can be casted in liquid state onto the surface delimited by the at least one further layer.

Further, the carrier may comprise edges that serve as a dam or dams when the materials of the first and second layer are casted onto the carrier successively in a liquid state.

Another variant for applying the walls is that all walls are realized together as one frame, which is fixed, in particular glued, to the carrier. Thereafter, the materials for the first and second layer are casted one after the other onto the surface delimited by the frame and cured.

BRIEF DESCRIPTION OF THE DRAWINGS

In the following, embodiments of the invention will be explained in more detail with reference to the accompanying drawings.

DETAILED DESCRIPTION OF ILLUSTRATIVE EMBODIMENTS

In the following detailed description, reference is made to the accompanying drawings, which form a part of this description and in which specific embodiments in which the invention may be practiced are shown for illustrative purposes. Since components of embodiments may be positioned in a number of different orientations, the directional terminology is for illustrative purposes and is in no way limiting. It is understood that other embodiments may be used and structural or logical changes may be made without departing from the scope of protection. It is understood that the features of the various embodiments described herein may be combined with each other, unless specifically stated otherwise. The following detailed description is therefore not to be understood in a restrictive sense. In the figures, identical or similar elements are given identical reference signs where appropriate.

Figure 3:
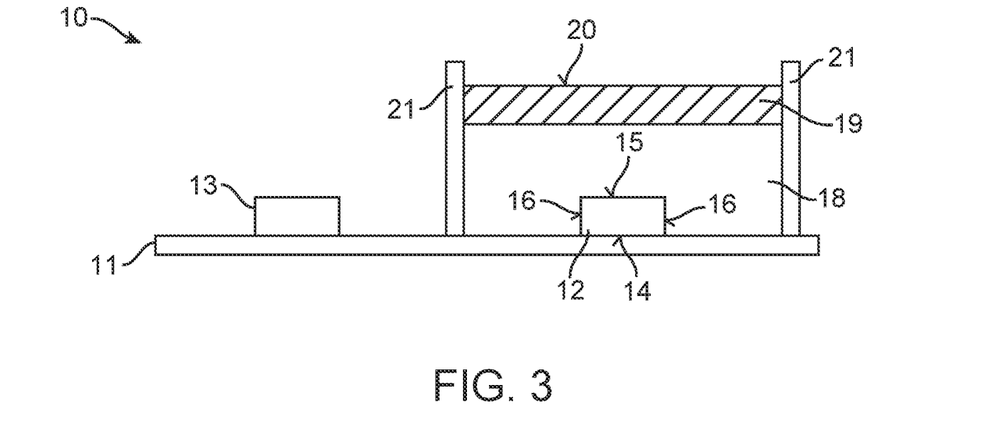
FIG. 3 is an illustration of an embodiment of a vital sign sensor.

FIG. 3 shows the schematic structure of a vital sign sensor 10, with which, for example, the heartbeat, heart rate or pulse of a user can be measured.

The vital sign sensor 10 comprises a carrier 11 in the form of a printed circuit board, on which an emitter component 12 in the form of an LED and a detector component 13 in the form of a photodiode are mounted.

The emitter component 12 comprises a first main surface 14 and a second main surface 15 opposite the first main surface 14, the first main surface 14 facing the carrier 11. A plurality of side surfaces 16 extend from the first main surface 14 to the second main surface 15.

The emitter component 12 is embedded in a first layer 18. In the present embodiment, the exposed portions of the second main surface 15 and the side surfaces 16 of the emitter component 12 are completely covered by the first layer 18. The first layer 18 consists of a substantially transparent, non-light-scattering material.

A second layer 19 of a light scattering material is deposited directly on the first layer 18. The second layer 19 contains scattering particles and/or phosphor particles that cause scattering of light emitted from the emitter component 12.

The second layer 19 comprises an upper exposed surface 20 through which the light exits. During operation of the vital sign sensor 10, the surface 20 faces the user's skin. The portion of the emitted light that reaches the detector component 13 is detected by the detector component 13.

Further, the vital sign sensor 10 comprises walls 21 extending upwardly from the carrier 11 and defining an intervening region in which the emitter component 12, the first layer 18, and the second layer 19 are arranged.

At least in the region where the wall 21 extends between the emitter component 12 and the detector component 13, the side of the wall 21 facing the emitter component 12 may be reflective and the side of the wall 21 facing the detector component 13 may be black.

Furthermore, the vital sign sensor 10 may comprise a control and evaluation unit not shown in FIG. 3. The control and evaluation unit can serve, on the one hand, to control the emitter component 12 and the detector component 13 in such a way that they emit or detect light, and, on the other hand, to evaluate the measurement signals received from the detector component 13 in order to determine therefrom, for example, the heartbeat rate of the user.

Figure 4:
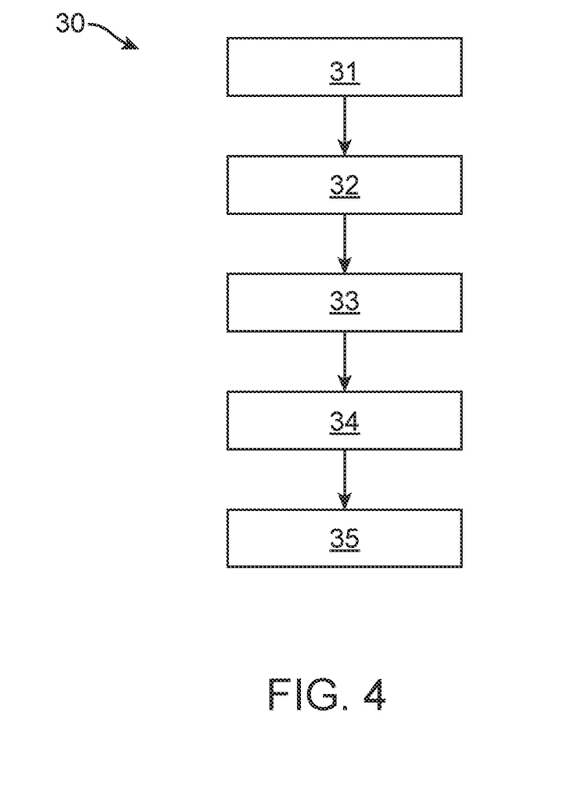
FIG. 4 is an illustration of an embodiment of a method for manufacturing a vital sign sensor.

FIG. 4 schematically shows a method 30 for manufacturing the vital sign sensor 10 of FIG. 3.

In step 31, the carrier 10, the emitter component 12 and the detector component 13 are provided.

In step 32, the emitter component 12 and the detector component 13 are mounted on the carrier 10 and electrically connected to conductor tracks of the carrier 10.

In step 33, the walls 21 are produced on the carrier 10.

In step 34, the first layer 18 is deposited on the surface delimited by the walls 21.

In step 35, the second layer 19 is deposited on the first layer 18.

Figure 5A:
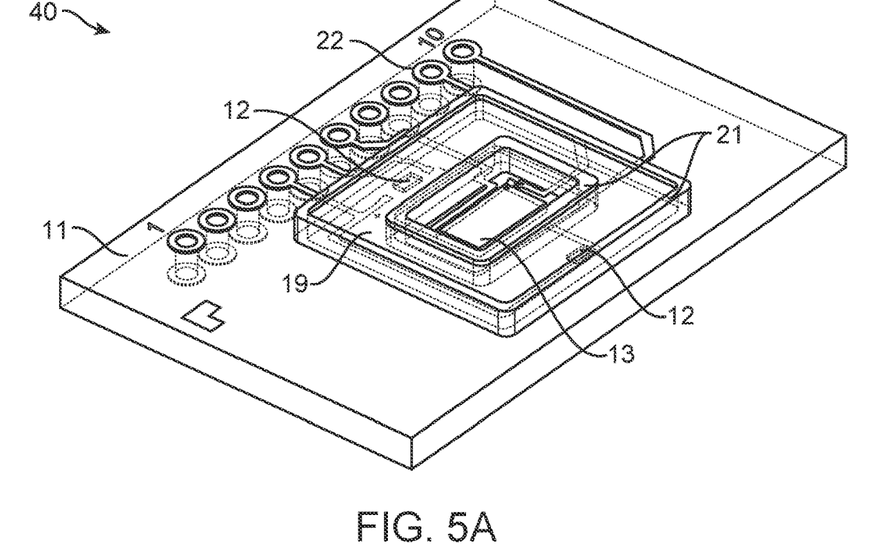
FIGS. 5A to 5C are an illustration of a further embodiment example of a vital sign sensor in various perspectives and sections.
Figure 5B:
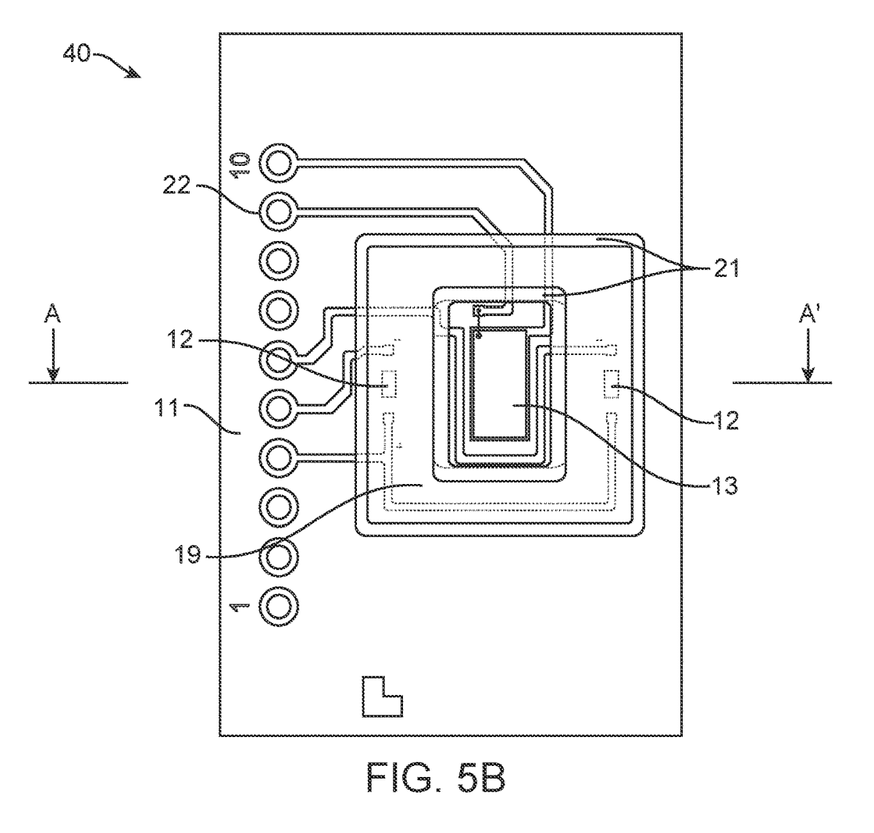
Figure 5C:
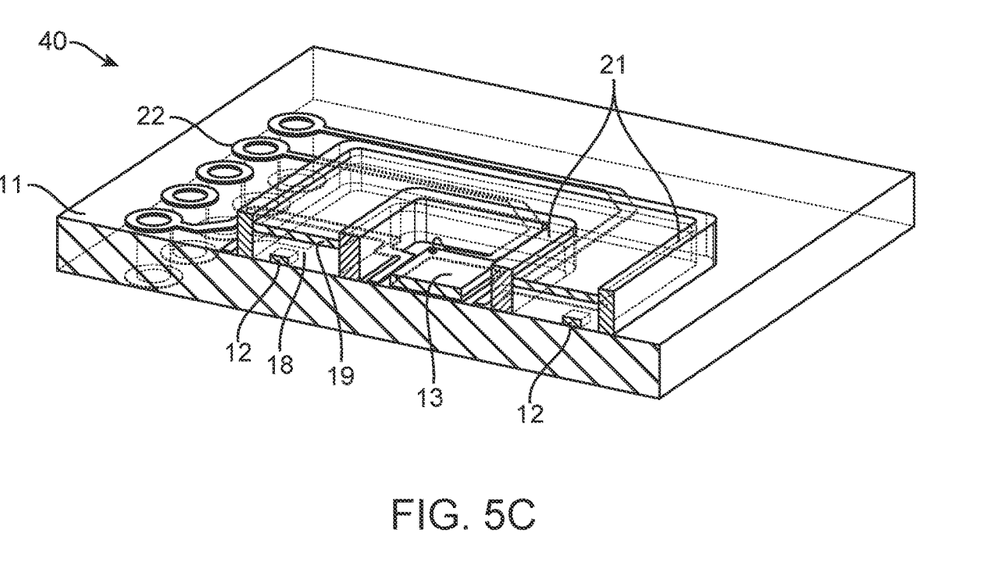

FIGS. 5A, 5B and 5C show the schematic structure of a vital sign sensor 40. FIG. 5A shows the vital sign sensor 40 in a perspective view. FIG. 5B shows the vital sign sensor 40 in a top view from above. FIG. 5D shows a section through the vital sign sensor 40 along the line A-A' shown in FIG. 5B.

The vital sign sensor 40 comprises a carrier 11 on which two emitter components 12 and a detector component 13 are mounted.

Further, walls or dams 21 are erected on the carrier 11 to form an outer ring and an inner ring located within the outer ring. The detector component 13 is located within the inner ring. The emitter components 12 are arranged in the area between the inner and outer ring. In this area, the first layer 18 of a transparent material and the second layer 19 of a light-scattering material are also deposited.

Furthermore, the vital sign sensor 40 comprises a plurality of contact elements 22 which are electrically connected to the emitter components 12 and the detector component 13 via conductor tracks. For example, a control and evaluation unit can be connected to the contact elements 22.

In the present embodiment, the carrier 11 is an FR4 board to which white solder resist is applied, which serves as a reflective material. The first layer 18 is made of highly refractive silicone with a refractive index of 1.55 and has a thickness of 0.7 mm. The second layer 19 has a thickness of 0.3 mm and contains low refractive index silicone with a refractive index of 1.42 with 40% weight concentration of a green emitting nitrido orthosilicate phosphor.

A white $TiO_2$-filled silicone was used for the walls 21. In the present embodiment, the walls 21 were applied in two steps. After the first step, clear encapsulation was performed to produce the first layer 18, and after the second step, converter encapsulation was performed to produce the second layer 19.

Alternatively, the walls 21 can be realized as one or more frames which are glued to the carrier 11 and into which the materials for the first layer 18 and the second layer 19 are casted successively.

The emitter components 12 are blue emitting sapphire chips with a size of 0.35 mm×0.7 mm. A Si photodiode with a size of 1.3 mm×2.7 mm was used as the detector component 13.

Although the invention has been illustrated and described in detail by means of the preferred embodiment examples, the present invention is not restricted by the disclosed examples and other variations may be derived by the skilled person without exceeding the scope of protection of the invention.

The invention claimed is:

1. A vital sign sensor comprising:
   an emitter component configured to emit light;
   a detector component configured to detect light;
   a first layer of a substantially transparent material, wherein the emitter component is embedded in the first layer; and
   a second layer of a light scattering material arranged on the first layer,
   wherein the second layer comprises converter particles,
   wherein the first layer and the second layer are surrounded by a wall of a reflective material, and
   wherein the wall forms a cavity in which the first layer and the second layer are entirely arranged.

2. The vital sign sensor according to claim 1, wherein the second layer comprises an exposed surface that is larger than a main surface of the emitter component.

3. The vital sign sensor according to claim 1, wherein the first layer comprises a higher refractive index than the second layer.

4. The vital sign sensor according to claim 1, wherein the light scattering material comprises non-light absorbing scattering particles.

5. The vital sign sensor according to claim 1, wherein the emitter component is mounted on a carrier and the carrier comprises a light reflective material.

6. The vital sign sensor according to claim 1, wherein the vital sign sensor comprises a plurality of emitter components configured to emit the light of a first wavelength spectrum.

7. The vital sign sensor according to claim 1, wherein the vital sign sensor comprises a further emitter component configured to emit light of a second wavelength spectrum.

8. The vital sign sensor according to claim 1, wherein the light scattering material comprises light scattering particles.

9. The vital sign sensor according to claim 1, wherein a further wall is arranged between the emitter component and the detector component, and wherein a side of the further wall facing the emitter component is reflective and a side of the further wall facing the detector component is black.

10. A wearable electronic device comprising:
    the vital sign sensor according to claim 1.

11. A method for manufacturing a vital sign sensor, the method comprising:
    providing an emitter component configured to emit light on a carrier;
    providing a detector component configured to detect light on the carrier;
    embedding the emitter component in a first layer of a substantially transparent material;
    arranging a second layer of a light-scattering material on the first layer; and
    providing a wall of a reflective material on the carrier, wherein the wall forms a cavity in which the first layer and the second layer are entirely arranged.

12. The method according to claim 11, further comprising mounting the emitter component and the detector component on the carrier before the emitter component is embedded in the first layer.

13. The method according to claim 12, wherein the emitter component is mounted on a light reflecting surface of the carrier.

14. The method according to claim 12, wherein the wall delimits a surface on the carrier and a material is casted onto the surface to form the first layer.

15. The method according to claim 14, further comprising, after providing the first layer, forming at least one further wall, wherein the at least one further wall delimits a further surface and a material is casted onto the further surface to form the second layer.

16. The method according to claim 12, wherein the wall delimits a surface on the carrier and a material is casted onto the surface to generate the first layer and subsequently a further material is casted onto the first layer to generate the second layer.

* * * * *